United States Patent
Prakash et al.

(10) Patent No.: US 6,952,265 B2
(45) Date of Patent: Oct. 4, 2005

(54) METHOD OF CHARACTERIZATION OF SURFACE COATING CONTAINING METALLIC FLAKES AND DEVICE USED THEREIN

(75) Inventors: Arun Prakash, West Chester, PA (US); Roger Albert Karmes, North East, MD (US); Judith Elaine Obetz, Newtown Square, PA (US); William B. Schenk, Avondale, PA (US); John P. Gallagher, Hockessin, DE (US); Allan Blase Joseph Rodrigues, Bloomfield Hills, MI (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 10/827,455

(22) Filed: Apr. 19, 2004

(65) Prior Publication Data

US 2004/0252308 A1 Dec. 16, 2004

Related U.S. Application Data

(60) Provisional application No. 60/477,875, filed on Jun. 12, 2003.

(51) Int. Cl.$^7$ .............................................. G01N 21/55
(52) U.S. Cl. ................................................... 356/445
(58) Field of Search ................................ 356/445–448, 356/405–407; 250/210, 306, 560

(56) References Cited

U.S. PATENT DOCUMENTS

| | | | | |
|---|---|---|---|---|
| 4,572,672 A | * | 2/1986 | Orchard et al. ............. | 356/446 |
| 4,711,580 A | * | 12/1987 | Venable ...................... | 356/406 |
| 4,802,763 A | * | 2/1989 | Gerlinger et al. ........... | 356/319 |
| 4,917,495 A | * | 4/1990 | Steenhoek ................... | 356/328 |
| 5,231,472 A | | 7/1993 | Marcus et al. | |
| 5,583,642 A | * | 12/1996 | Nakazono .................... | 356/405 |
| 5,963,334 A | * | 10/1999 | Yamaguchi et al. ......... | 356/425 |
| 5,965,272 A | | 10/1999 | Donnelly et al. | |
| 6,166,814 A | | 12/2000 | Pringle | |
| 6,437,865 B1 | | 8/2002 | Willing | |
| 6,451,930 B1 | | 9/2002 | Burgman et al. | |
| 2002/0184168 A1 | | 12/2002 | McClanahan et al. | |
| 2002/0184171 A1 | | 12/2002 | McClanahan et al. | |

* cited by examiner

Primary Examiner—Michael P. Stafira
(74) Attorney, Agent, or Firm—Sudhir G. Deshmukh (57) ABSTRACT

The method of present invention and the device used therein is directed for characterizing unknown metallic flakes present in an existing coating on a substrate such that a matching metallic paint composition can be formulated and applied over the substrate to produce a metallic coating having characteristics, such as flop, that match the existing coating. The method includes directing a beam of light at a preset intensity towards a target portion of a target coating; directing a reflection of the portion to a photosensitive surface to capture a target image of the target portion; measuring characteristics of the unknown metallic flakes in the target image at said preset intensity; correlating the characteristics of the unknown metallic flakes in the target image to stored characteristics of known metallic flakes at that preset intensity to identify one or more the known metal flakes that match the characteristics of the unknown metallic flakes; and displaying the identified one or more known metal flakes that match the characteristics of the unknown metallic flakes. Once the characteristics are known, a formulator can then formulate a metallic paint that can be applied over the surface of a substrate, such as a repaired autobody, to produce a metallic coating that matches the remainder of the autobody.

52 Claims, 5 Drawing Sheets

Higher Threshold

Lower Threshold

METHOD OF CHARACTERIZATION OF SURFACE COATING CONTAINING METALLIC FLAKES AND DEVICE USED THEREIN

CROSS REFERENCE TO RELATED APPLICATION

This application claims priority under 35 U.S.C. §119 from U.S. Provisional Application Ser. No. 60/477,875, filed Jun. 12, 2003, which is incorporated by reference herein as if fully set forth.

FIELD OF INVENTION

The present invention generally relates to a method of characterizing surface coatings containing metallic flakes and to a device used therefor. The method is especially suited for characterizing unknown metallic flakes used in automotive refinish coating compositions.

BACKGROUND OF THE INVENTION

Surface coatings containing a metallic flake pigment, for example aluminum flake, are well known. They are especially favored for the protection and decoration of automobile bodies, such as for example by reason of their imparting a differential light reflection effect, usually referred, to as "flop", as well as flake appearance effects, which include flake size distribution and the sparkle imparted by the flake as well as the enhancement of depth perception in the coating. The flop effect is dependent upon the angle from which the car body is viewed. The degree of the flop effect achieved, is a function of the orientation of the metallic flakes with respect to the outer surface of the coating. To attain a maximum flop effect, ideally, the flakes should all lie in planes parallel to this surface. However, in practice it is not possible to obtain more than a proportion of the flakes lying truly parallel, the remainder lie at various angles to the surface plane, i.e. there is a distribution of the orientations of the metallic flakes in the coating. The degree of sparkle is a function of the flake size, surface smoothness, orientation, and uniformity of the edges. Metallic coatings usually also contain pigments, generally of a light absorbing rather than a light scattering type. Any light scatter from the pigments or the flakes themselves, e.g., from the flake edges, diminishes both the flop and the sparkle of the coating.

Instrumental characterization of metallic pigmented coatings can, in principle, be carried out by measuring with a spectrophotometer the spectral reflectance of a coated panel at a number of angles of incident illumination and of viewing, either within the plane of the illumination and viewing axes, or outside of this plane. The results of such measurements are dependent on the degree of flake alignment as well as the type of flake or other pigments used, but give no direct evidence of the degree of sparkle or flake size. As a result, their value in characterizing the coating is insufficient. Additionally, since these measurements are also dependent on the relative concentrations of the metallic flake and on the presence or absence of any light-absorbing or scattering pigment in coating composition, their value in characterizing the coating is diminished. In color matching for example a previously coated substrate of an automotive body, it is necessary to choose the correct pigments to match the color of that substrate as well as the correct flake to match the color and appearance of that substrate. For an effective measure of the flake characteristics such as size or degree of sparkle of the metallic flakes to be obtained, therefore, it is necessary under these circumstances for shaders to select, based on their expertise, the metallic flake to be used by visually analyzing the target surface, such as a previously coated substrate of an automotive body. Once the flake has been identified, the pigments are selected, typically by well known computer based algorithms, such as those based on radiative transfer theory, which mathematically adjust the pigment quantities, add or reduce black and white pigment quantities, and flop adjuster quantities, including flake quantities, so that the error in the color and flop match to the target surface is the lowest while ensuring that the resulting color/flop formulation is still within the bounds of accepted commercial practice. This formulation is then made up, sprayed on test panels, which are then visually compared to the target surface. If the flop and/or sparkle match are deemed unsatisfactory, the shader adjusts the type and/or changes the amount of the metallic flakes entered into the algorithm to get new color/flop formulation and the whole cycle is repeated until an adequate match is achieved in both color and appearance at all angles of illumination and view. The present invention is aimed at a method that substantially reduces the number of repeat matches needed for the selection of metallic flakes that closely match the appearance of metallic flakes present in the target surface.

STATEMENT OF THE INVENTION

The present invention is directed to a device for characterizing a target coating containing unknown metallic flakes comprising:

(i) means for positioning said device over said target coating;
(ii) means for producing one or more beams of light at one or more preset intensities;
(iii) means for imaging;
(iv) means for directing said beams of light towards a target portion of said target coating;
(v) means for directing a reflection of said target portion to a photosensitive surface located in said means for imaging to capture a target image of said portion;
(vi) means for measuring characteristics of said metallic flakes in said target image at said preset intensity;
(vii) means for correlating said characteristics of said unknown metallic flakes in said target image to stored characteristics of known metallic flakes at said preset intensity to identify one or more said known metal flakes that match said characteristics of said unknown metallic flakes; and
(viii) means for displaying said identified one or more known metal flakes that match said characteristics of said unknown metallic flakes.

The present invention is directed to a method for characterizing a target coating containing unknown metallic flakes comprising:

(i) directing one or more beams of light at a preset intensity towards a target portion of said target coating;
(ii) directing a reflection of said portion to a photosensitive surface to capture a target image of said target portion;
(iii) measuring characteristics of said unknown metallic flakes in said target image at said preset intensity;
(iv) correlating said characteristics of said unknown metallic flakes in said target image to stored characteristics of known metallic flakes at said preset intensity to identify one or more said known metal flakes that match said characteristics of said unknown metallic flakes; and
(v) displaying said identified one or more known metal flakes that match said characteristics of said unknown metallic flakes.

The present invention is more particularly directed to a method for characterizing a target coating containing unknown metallic flakes comprising:

(i) directing sequentially a collimated beam of light at three preset intensities upon a target portion of said target coating at a normal angle;
(ii) directing a reflection of said coated surface to a photosensitive surface to sequentially capture images in a gray scale of said target portion at said preset intensities at said three preset intensities;
(iii) sequentially measuring characteristics of said unknown metallic flakes in said target images;
(iv) correlating said characteristics of said unknown metallic flakes in said target images to benchmark characteristics of known metallic flakes at said preset intensities to identify three said known metal flakes that match said characteristics of said unknown metallic flakes;
(v) displaying said identified one or more known metal flakes that match said characteristics of said unknown metallic flakes.

The present invention is also directed to a method for producing a metallic flake containing coating composition, wherein a coating therefrom matches characteristics of a target coating containing unknown metallic flakes, said method comprising:
(i) directing one or more beams of light at a preset intensity towards a target portion of said target coating;
(ii) directing a reflection of said portion to a photosensitive surface to capture a target image of said target portion;
(iii) measuring characteristics of said unknown metallic flakes in said target image at said preset intensity;
(iv) correlating said characteristics of said unknown metallic flakes in said target image to stored characteristics of known metallic flakes at said preset intensity to identify one or more said known metal flakes that match said characteristics of said unknown metallic flakes;
(v) displaying said identified one or more known metal flakes that match said characteristics of said unknown metallic flakes;
(vi) preparing one or more test coating compositions containing said identified known metal flakes;
(vii) applying said test coating compositions over test substrates to produce test coatings thereon;
(vii) comparing said test coatings against said target coating to select test coating having characteristics that match said characteristics of said target coating; and
(viii) selecting test coating composition that produces said matched test coating.

DETAILED DESCRIPTION OF THE PREFERRED EMBODIMENT

As used herein:

"Pixel" means the smallest discrete element of a photosensitive surface of an imaging device that can detect multiple levels of light intensities either in gray scale, in three primary colors (red, green and blue; or red, yellow and blue), or both.

"Flop adjustor" means an additive or additives in a metallic coating composition that disrupts the orientation of metallic flakes. Some typical flop adjustors are glass beads or silica and titanium dioxide pigment.

"Characteristics of flakes" means the size, amount, and type of metallic flakes that are incorporated in metallic coating composition to provide the desired sparkle to a coating resulting therefrom. In addition to the metallic flakes, the coating generally includes polymers, special effect flakes, pigments, and additives. Moreover, the metallic coatings often also contain pearlescent flakes, whose appearance is caused by light interference effects. Typically, conventional pigments include light absorbing pigments, light scattering pigments, light interference pigments, light reflecting pigments, or a combination thereof. Some suitable pigments include metallic oxides, such as titanium dioxide, zinc oxide, iron oxides of various colors; carbon black; filler pigments, such as talc, china clay, barytes, carbonates, silicates; and a wide variety of organic colored pigments, such as quinacridones, copper phthalocyanines, perylenes, azo pigments, indanthrone blues, carbazoles, such as carbozole violet, isoindolinones, isoindolones, thioindigo reds and benzimidazolinones.

The present invention is directed to a method and a device suitable for characterizing a coating containing conventional metallic flakes. The coating is typically applied over a substrate, such as an automotive body.

Figure 1:
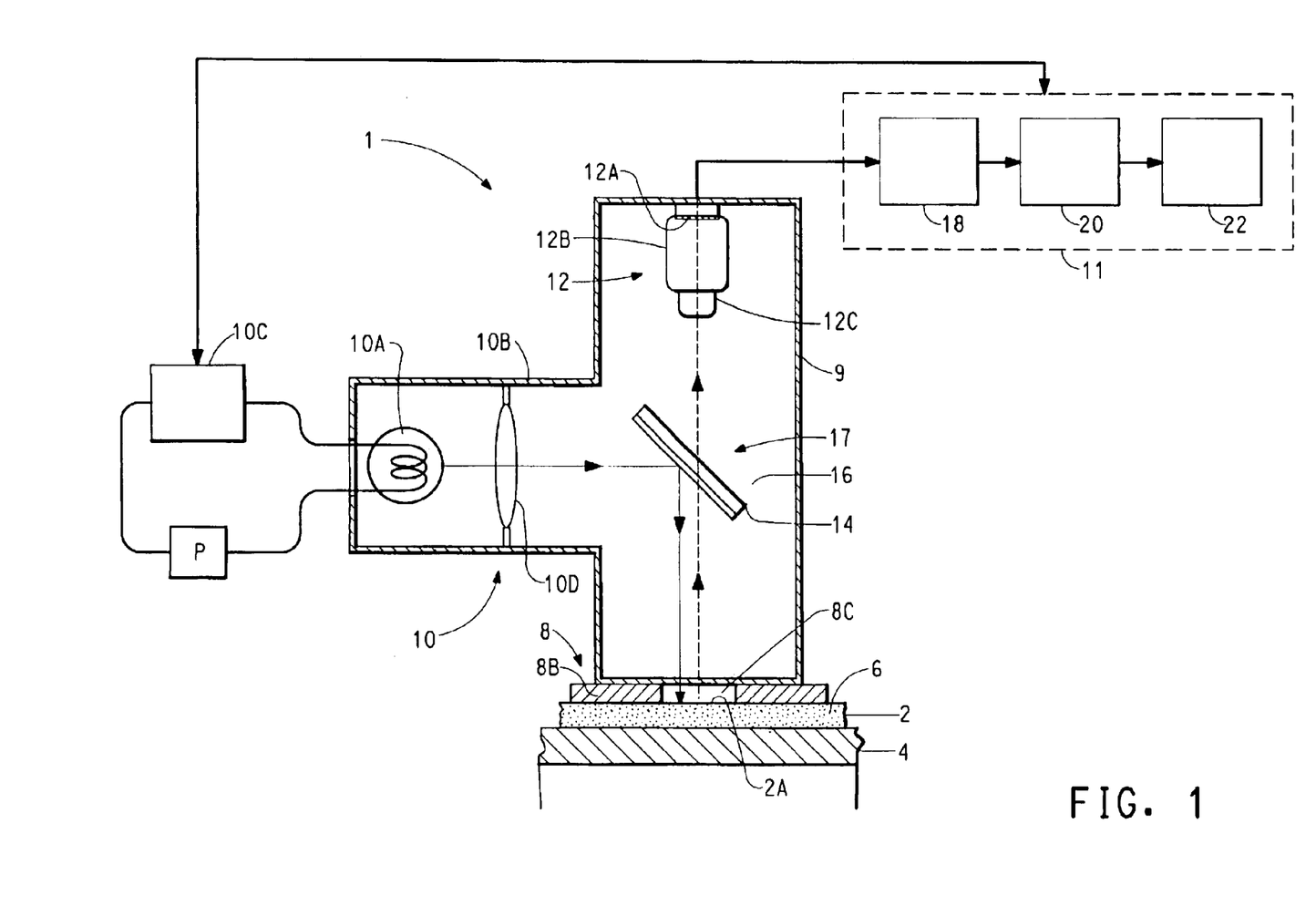
FIG. 1 is a diagrammatic representation of a device of the present invention.

FIG. 1 illustrates the broadest aspects for a device 1 of the present invention. A target coating 2 containing unknown metallic flakes 6 is applied over a substrate 4, such as an automotive body.

Device 1 in its broadest aspect includes means 8 for positioning device 1 over target coating 2, means 10 for producing one or more beams of light at one or more preset intensities, means 12 for imaging; means 14 for directing said beams of light towards a target portion 2A of target coating 2, means 16 for directing a reflection of target portion 2A to a photosensitive surface 12A located in means 12 for imaging to capture a target image of target portion 2A, means 18 for measuring characteristics of unknown metallic flakes 6 in the target image at the preset intensity, means 20 for correlating the characteristics of unknown metallic flakes 6 in the target image to stored characteristics of known metallic flakes at the preset intensity to identify one or more the known metal flakes that match the characteristics of unknown metallic flakes 6 and means 22 for displaying the identified one or more known metal flakes that match the characteristics of unknown metallic flakes 6.

Referring now to the more detailed aspect of Device 1, one of the embodiments of means 8 for positioning target coating 4 includes a substantially flat base 8B, which preferably forms a part of a housing 9 of device 1. Base 8B is provided with an aperture 8C, which is preferably shielded with a transparent panel, such as that made of glass for protecting the components of device 1 positioned inside housing 9 from external damage or from dust. Aperture 8C is preferably circular. However, other shapes, such as a square shape or a rectangular shape can also be employed. Aperture 8C, preferably has a diameter ranging from 0.01 mm to 25 mm. Diameter of about 2 mm (¼") is preferred. The exposed surface of base 8B is preferably kept in intimate physical contact with the target portion 2A to keep photosensitive surface 12A in focus. It is within the contemplation of this invention to attain the intimate contact of base 8B to the surface of substrate 2 by magnetizing base 8B when used with steel substrate. Alternatively, a plurality of conventional clamps or suction cups could also be employed.

Means 10 for producing one or more beams of light at one or more preset intensities typically include a light source 10A, such as, the IT3900 with a tungsten-halogen lamp EKE supplied by Illumination Technologies Inc., East Syracuse, N.Y. and a fiber optic bundle A08025.60 supplied by Schott Fostec Inc., Auburn, N.Y. that is capable of producing beams of light in the visible light range of from 400 nanometers to 700 nanometers at set intensities. Device 1, which is preferably portable, is preferably provided with an enclosed extension 10B to house light source 10A. However, applicants also contemplate using alternative means, such as the MHF-C50LR light source with an LM-50 lamp and a fiber optic bundle connected to a MML4-45D micro machine lens system, supplied by Moritex USA Inc., San Jose, Calif. to pipe-in the light beams from light source 10A. The intensity of light source 10A can be controlled by conventional means, such as a voltage regulator 10C that can change the current to the filament of light source 10A in accordance with a conventional software program run from a computer 11 to achieve the preset intensities, typically set at three levels ranging, for the lowest level, from 2% to 96% of illumination levels, based on the brightest level possible from light source 10A, provided these levels differ from one another by at least 2%. Any suitable computer can be used, such as, for example, Dell Precision M50 model supplied by Dell Computer Corp., Round Rock, Tex. If desired, means 10 can further include means 10D, such as a collimating lens or an aperture, for collimating the one or more beams of light emanating from light source 10A. One possible approach is shown in FIG. 1, wherein the position of light source 10A coincides with focal point of means 10D in the form of a collimating lens.

Means 12 for imaging, which are preferably located opposite means 8 for positioning in housing 9 include an imaging device 12B, such as a video or a digital camera that includes photosensitive surface 12A for capturing the target image of target portion 2A. Photosensitive surface 12A can be a charged couple device sensor of a camera that produces the target image. Imaging device 12B is suitable for producing images in gray scale, in color or in both, such that the target image is captured either as a gray target image or as a color image. Gray target image is preferred. One suitable imaging device 12B is Pulnix® 7EX video camera supplied by Pulnix Inc., Sunnyvale, Calif. that produces gray scale images. Typically, a footprint of the gray or color target images capable of being produced by imaging device 12B range from about 0.01 millimeters square to about 25.0 millimeters square, preferably from about 0.25 millimeters square to 4 millimeters square, more preferably from about 0.5 millimeters square to 2. 0 millimeters square, and most preferably the footprint is a 1.5 millimeters square. Typically, imaging device 12B is capable of digitizing the gray or color target image of target portion 2A imaging device 12B in the range of from 40,000 pixels to 16,000,000 pixels (640×480), wherein each pixel is capable of recognizing light intensities ranging from 16 to 65,536 levels for each of three primary color channels when the target image is in color. The applicants have discovered that pixels capable of recognizing about 256 levels of light intensities are adequate for use in Device 1, since recognition of additional levels of intensities beyond 256 by the pixels would only be of marginal improvement while the cost of imaging device 12B would be prohibitively high.

Means 14 for directing said beams of light towards a target portion 2A of target coating 2 and means 16 for directing the reflection of target portion 2A to photosensitive surface 12A located in means 12 together preferably form a conventional beam splitter 17, which is essentially a two-way mirror. The two-way mirror beam splitters are well known, which typically include a reflective thin film of, for example, gold deposited on a transparent substrate, such as of glass. Beam splitter 17 is preferably positioned between means 8 and means 12 in such a way (typically at about 45 degrees, as shown in FIG. 1) that an incident beam of light (shown as a solid line in FIG. 1) from means 10 positioned adjacent to beam splitter 17 is reflected by the reflective film at an angle normal to target portion 2A but a reflected beam of light (shown as a dotted line) reflected from target portion 2A is transmitted through the transparent substrate to means 12. In the aforedescribed beam splitter 17, means 14 forms the reflective film and means 16 forms the transparent substrate.

Figure 2:
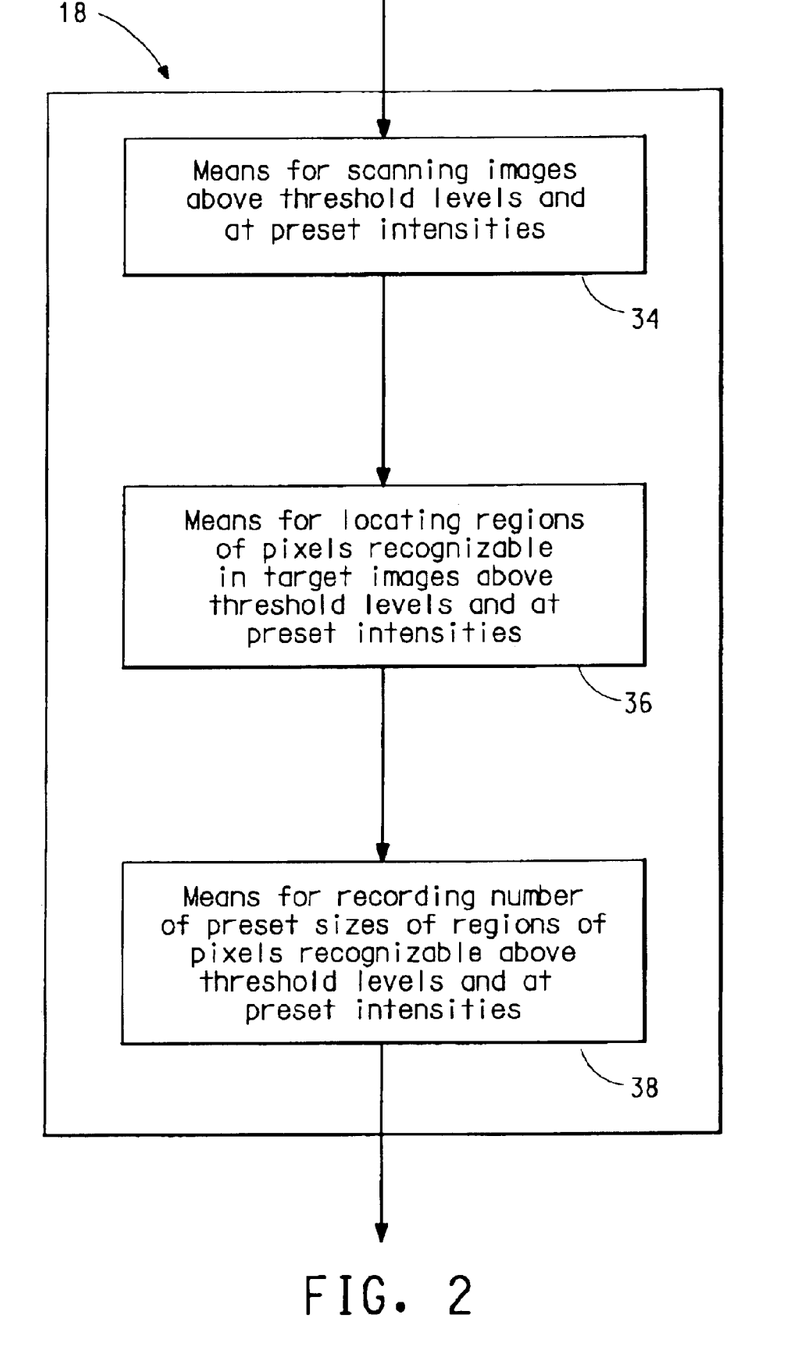
FIG. 2 is a flow chart for performing the tasks employed in means for measuring characteristics of metallic flakes at a preset intensity in a target image of a portion of a target coating containing unknown metallic flakes.

FIG. 2 shows the details of means 18 for measuring characteristics of unknown metallic flakes 6 represented by the regions of pixels that match the contours of the unknown flakes in the target image at the preset intensity. The software portion of means 18 is loaded on computer 11 of device 1. Any suitable software writing program could be used such as, for example, Visual C++ platform Version 6.0, operating on WindowsR 2000 operating system all supplied by Microsoft Corporation, Redmond, Wash. Means 18 include means 34 for scanning the target images above threshold levels at the preset intensities. Means 34 include conventional means for scanning the target images and a software program needed to measure the characteristics of unknown metallic flakes 6 represented by the corresponding regions of pixels in the target image. For the purposes of this invention, the threshold level, which can be set at a desired level, is defined as that level at the preset intensity below which any features present in the scanned image of the target image are not recognized. It should be understood that a feature of the metallic flake, such as its size, in the scanned image of the target image that was not recognized at a higher threshold level could be recognized at another lower threshold level. Applicants have discovered that when the threshold levels are set at several threshold levels, such as for, example, 150, 130, 110, 90 and 70 almost all the necessary features of unknown metallic flakes 6 can be extracted. The higher the threshold level, the fewer will be the features recognized in the scanned image, since at the higher threshold levels, only the most prominent features of unknown metallic flakes 6 would be recognized. Means 18 also include means 36 for locating regions of pixels recognizable in the target images above the threshold levels and at said preset intensities. By locating the regions of pixels in the target image, a grid map of these regions is developed for further analysis. Means 18 further include means 38 for recording the number of preset sizes of the regions of pixels recognizable above the threshold levels at the preset intensities. Such preset sizes of regions of pixels are preferably divided into small, medium, large, extra large zones, clusters of zones, or a combination thereof. As mentioned earlier, these zones represent a scanned representation of unknown metallic flakes 6 in target coating 2. Preferably, the small zones range from about 49 to about 83 micrometers square, the medium zones range from about 127 to about 239 micrometers square, the large zones range from about 342 to about 576 micrometers square, the extra large zones range from about 577 to about 122500 micrometers square, and the cluster zones range from about 49 micrometers square to about 122500 micrometers square.

The foregoing steps in means 18 are repeated at additional threshold levels at each of the additional preset intensities. As a result, means 18 extract from the target image, at each of the preset intensities, the total number of regions of pixels of the preset sizes utilizing several threshold levels. By way of example, the steps in means 18 are performed at three preset intensities of 19.6%, 31.4% and 39.2% illumination levels based on the brightest illumination level possible and in each of these preset intensities, the target images are scanned at threshold levels of 150, 130, 110, 90 and 70.

Once the flake characteristics of unknown flakes 6 are determined in means 18, device 1 provides for means 20 for correlating the characteristics of unknown metallic flakes 6 in the target images to benchmark characteristics of known metallic flakes at the preset intensities to identify three known metal flakes that match the characteristics of unknown metallic flakes 6. Thus, matching the characteristics of unknown metallic flakes 6 with those of known metallic flakes, which are stored in means 20, three best choices, which are the closest to the characteristics of unknown metallic flakes 6, are provided. The formulator is then able to produce a metallic paint that produces a coating having metallic flake characteristics that match the metallic flake characteristics of coating 2. The formulator can then visually select the metallic paint that produces a coating that most closely matches target coating 2 containing unknown metallic flakes 6. It is understood that depending upon the intended selection process, device 1 can be programmed to set the selection to more or less than three closest matches described above.

Figure 3A:
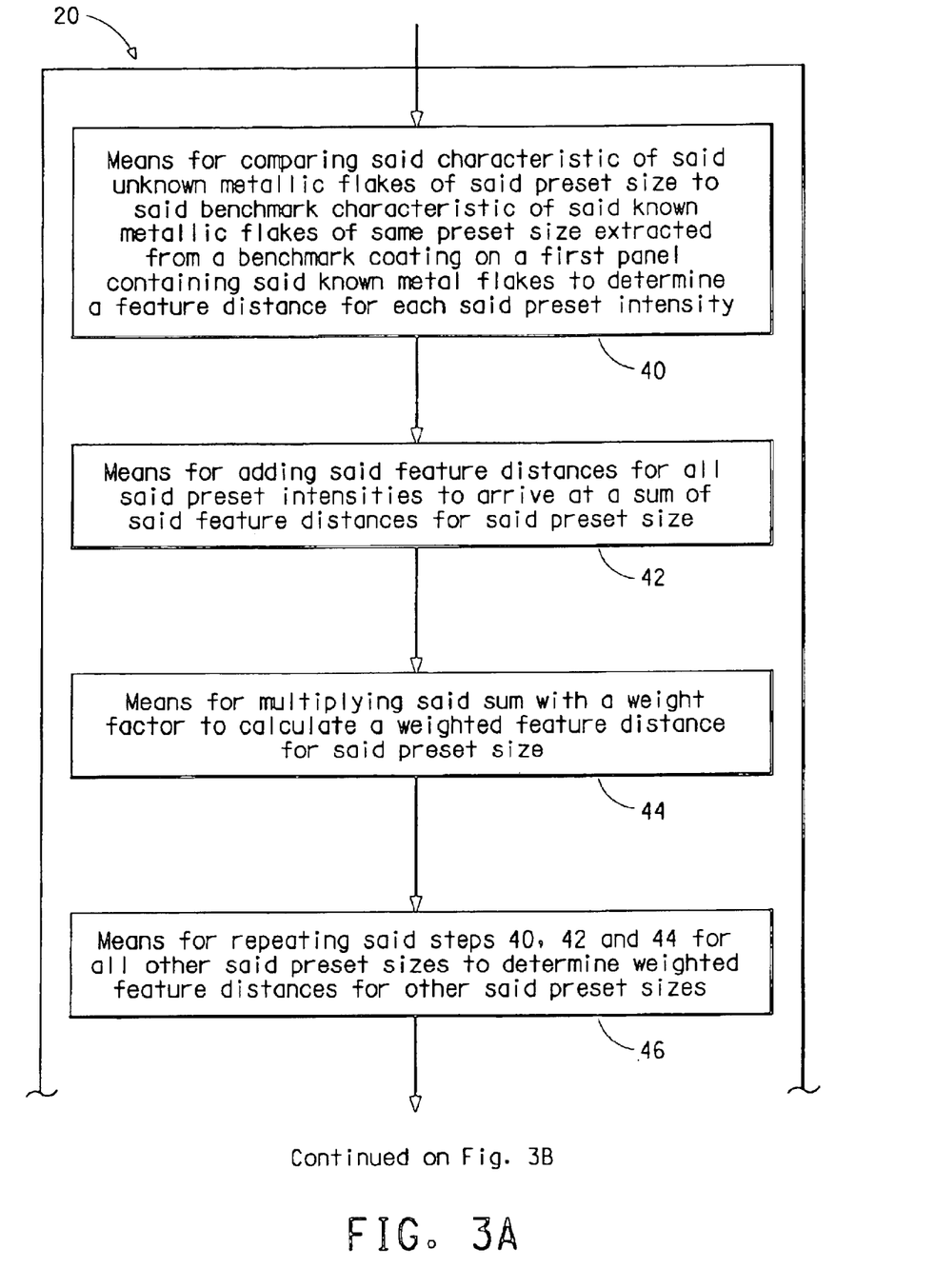
FIG. 3 is a flow chart of some of the means for performing tasks employed in means for measuring characteristics of the unknown metallic flakes in the target image at the preset intensity.
Figure 3B:
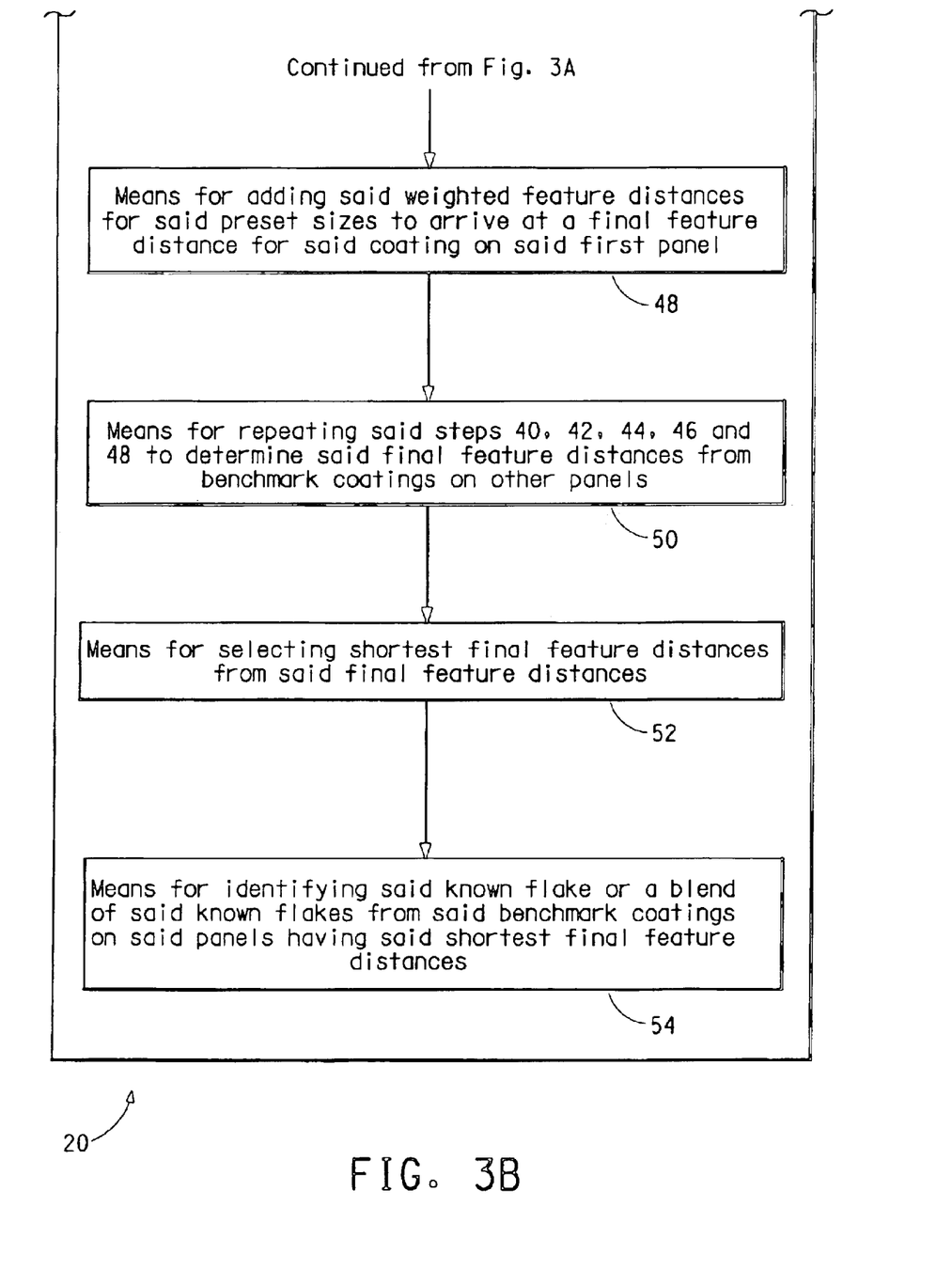
Figure 4:
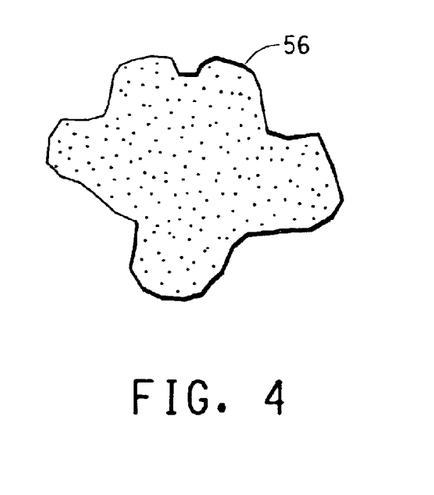
FIGS. 4, 5, 6 and 7 are representations regions of pixels of the target images of the unknown metallic flakes at different threshold levels.

As seen in FIG. 3, means 20 include:

(a) Means 40 for comparing the characteristic of unknown metallic flakes 6 of the preset size to the benchmark characteristic of the known metallic flakes of same preset size extracted from a benchmark coating on a first panel containing the known metal flakes to determine a feature distance for each preset intensity. The feature distance is a metric that quantifies how visually alike the sparkle characteristics of two panels is. The raw sparkle characteristics are the number of flakes exhibiting sparkle within the small, medium, large and extra large size of pixels at each of the three illumination levels. There are thus 12 raw sparkle features associated with any flake type on a painted panel. When comparing the sparkle characteristics of two panels, a raw feature value from one panel is compared to its respective feature value from the other panel and a feature distance for those feature values is computed by using, for example, the matrix shown below. In the matrix, the first row (all in bold) contains the feature distances from 0.0 to 10.0 and the remaining rows represent raw feature values. One starts by choosing the smallest of the feature values from the two panels and identifies the row within the first column that corresponds to it. For example, if the feature value for a first panel is 2 and the corresponding feature value for the second panel is 4; then, one would look up column 1 to locate that feature value (see Row 4 and Column 1) and then look up the column within row 4. which would have the feature value of the second panel. This is in column 3 within row 4. Lastly, one would read the feature distance at top of column 3. Thus, the feature distance would be 1.0 represented. Similarly, if a feature value for the first panel is 2.5 and for the second panel is 8.0, one would recognize that the feature value of 2.5 would have to be interpolated as it falls between rows 4 and 5 when looked up in column 1 for the first panel. Within this interpolated row (between rows 4 and 5) one would search for the second feature value, which is 8.0. This would likely be between columns 6 and 7 of the interpolated row. Thus, the feature distance would be between columns 6 and 7 of the feature distance row i.e. between 4.0 and 5.0. If the feature values fall outside of the matrix shown in Table 1 below, one can readily find the feature distances for such feature values by linear extrapolation. For example, if the feature value for the first panel is 40.5 and the corresponding feature value for the second panel is 24.2, then one first selects the smaller feature value i.e. 24.2. Since this value is higher than the highest entry in column 1 of the matrix of Table 1, one first linearly extrapolates from the last row i.e. row 14, to create a new row in which the first entry would be 24.2. The linear extrapolation in this case is enabled by multiplying each term of row 14 by a factor of resulting from dividing 24.2 by 12 (approximately 2.02). Then, in the extrapolated row at column 5 the feature value would be 36.3 (18.0×2.02) and column 6 the feature value would be 42.35 (21.0×2.02). The second feature value (40.5) will then likely falls between column 5 and 6 of this extrapolated row. Thus, the feature distance would be between 4.0 to 5.0.

This "feature distance" is computed in the software in means 20 and it is used for predicting the features of known flakes, such as flake size that matches the features of unknown flakes that are represented by the regions of pixels that correspond to the unknown flakes in target portion 2A. Thus, if "d" is the distance for the features, in means 40, such a distance is measured for each preset intensity level (for example, 19.6%, 31.4% and 39.2%) for each preset size described earlier, which are small ($d^a_1$, $d^b_1$, $d^c_1$), medium $d^a_2$, $d^b_2$, $d^c_2$), large ($d^a_3$, $d^b_3$, $d^c_3$), and extra large ($d^a_4$, $d^b_4$, $d^c_4$). In the foregoing, the superscripts represent the preset intensities for each preset sizes. Thus, a =19.6%, b=31.4 and 39.2%)

TABLE 1

| | Feature Distances | | | | | | |
|---|---|---|---|---|---|---|---|
| 0.0 | 0.5 | 1.0 | 2.0 | 3.0 | 4.0 | 5.0 | 10.0 |
| | | | Feature Values | | | | |

| Rows | Col. 1 | Col. 2 | Col. 3 | Col. 4 | Col. 5 | Col. 6 | Col. 7 | Col. 8 |
|---|---|---|---|---|---|---|---|---|
| 1 | 0.0 | 1.5 | 2.0 | 3.0 | 4.0 | 5.0 | 6.0 | 12.0 |
| 2 | 0.5 | 2.0 | 2.5 | 3.5 | 4.5 | 5.5 | 6.5 | 13.0 |
| 3 | 1.0 | 2.5 | 3.0 | 4.0 | 5.0 | 6.0 | 7.0 | 13.5 |
| 4 | 2.0 | 3.5 | 4.0 | 4.8 | 5.7 | 6.7 | 7.8 | 14.0 |
| 5 | 3.0 | 4.5 | 5.5 | 6.5 | 7.2 | 8.0 | 9.0 | 15.0 |
| 6 | 4.0 | 5.6 | 6.3 | 7.5 | 8.5 | 9.3 | 10.7 | 18.4 |
| 7 | 5.0 | 6.8 | 7.5 | 8.8 | 9.9 | 10.6 | 12.4 | 21.8 |
| 8 | 6.0 | 7.8 | 8.6 | 9.8 | 11.0 | 12.0 | 14.1 | 24.6 |
| 9 | 7.0 | 8.8 | 9.7 | 10.8 | 12.0 | 13.5 | 15.8 | 27.7 |
| 10 | 8.0 | 9.8 | 10.7 | 11.8 | 13.1 | 15.0 | 17.4 | 30.4 |
| 11 | 9.0 | 10.8 | 11.8 | 13.0 | 14.3 | 16.5 | 18.9 | 33.3 |
| 12 | 10.0 | 11.9 | 12.9 | 14.2 | 15.5 | 17.9 | 20.5 | 36.0 |
| 13 | 11.0 | 12.9 | 14.0 | 15.3 | 16.7 | 19.5 | 22.2 | 39.1 |
| 14 | 12.0 | 13.8 | 15.0 | 16.5 | 18.0 | 21.0 | 24.0 | 42.0 |

(b) means 42 for adding the feature distances for all the preset intensities to arrive at a sum of the feature distances for the preset size. Thus, the following equation represents the calculations taking place in means 42:

$$d_1 = d^a_1 + d^b_1 + d^c_1$$

(c) Means 44 for multiplying the sum ($d_1$) with a weight factor ($w_1$) to calculate a weighted feature distance for the preset size. In general, the weight factors are chosen for each size based on the visual importance to be given to each feature, such as its size. Thus, the higher the weight factor, the higher will be the visual importance of that preset size. In the present invention, applicants have opted to use $w_1=0.4$, $w_2=0.6$, $w_3=0.8$, and $w_4=1.0$ (d) Means 46 for repeating said steps 40, 42 and 44 for all other said preset sizes to determine weighted feature distances for other said preset sizes. Thus, the following equations represent the calculations taking place in means 46:

$$d_2 = d^a_2 + d^b_2 + d^c_2$$
$$d_3 = d^a_3 + d^b_3 + d^c_3$$
$$d_4 = d^a_4 + d^b_4 + d^c_4$$

followed by $$d_2 \times w_2$$
$$d_3 \times w_3$$
$$d_4 \times w_4$$

(e) Means 48 for adding the weighted feature distances for the preset sizes to arrive at a final feature distance for the coating on the first panel:

$$d = d_1 \times w_1 + d_2 \times w_2 + d_3 \times w_3 + d_4 + w_4$$

(f) Means 50 for repeating said steps 40, 42, 44, 46 and 48 to determine the final feature distances from benchmark coatings on other panels. Thus, the final feature distance (d) is also determined from other benchmark coatings on other panels.

(g) Means 52 for selecting shortest final feature distances from the final feature distances. Once all the final feature distances are determined, those (d)s which are shortest are selected in means 52. Typically, about three shortest final feature distances (d) are selected.

(h) Means 54 for identifying the known flake or a blend of the known flakes from the benchmark coatings on the panels having the shortest final feature distances. Means 54 provides the formulator the metallic compositional details needed to produce a metallic coating that matches the sparkle, color and flop of target coating 2.

In means 40 described above, the characteristics of unknown metallic flakes 6 at each preset size are compared with the benchmark characteristics of the known metallic flakes of the same preset size. The benchmark characteristics of the known metallic flakes are measured by using Device 1 for a series of coated panels having various combinations of known metallic flakes. The benchmark characteristics of the known metallic flakes are stored in the memory of computer 11.

The present invention is also directed to a method for characterizing target coating 2 containing unknown metallic flakes 6. The method includes the following steps:

(i) Directing one or more beams of light at a preset intensity towards target portion 2A of target coating 2. These beams of light are produced by means 10 from light source 10A. These beams are preferably collimated by means 10D. Additionally, the beams are directed at a perpendicular, i.e., normal, angle to the surface of target portion 2A. However, though a normal angle is preferred, an angle within the range from 85° to 95° would be also suitable for use in the present invention. Preferably, one or more beams of light are directed sequentially at plurality of preset intensities, preferably at at least two, and more preferably at least three preset intensities described earlier.

(ii) Directing a reflection of target portion 2A to photosensitive surface 12A to capture a target image in color or preferably in gray scale, of target portion 2A. Preferably, one or more reflections of target portion 2A are directed sequentially at plurality of other preset intensities to photosensitive surface 12A.

(iii) Measuring characteristics of unknown metallic flakes 6 in the target image at the preset intensity. Preferably, characteristics of unknown metallic flakes 6 in the target image are sequentially measured at a plurality of other preset intensities. The foregoing step (iii) includes several of the following sub-steps:

(a) scanning the target images at first of the preset intensities and at first of threshold levels;

(b) locating regions of pixels recognizable above the first threshold level in the target images at the first of the preset intensities;

(c) scanning the target images at the first of the preset intensities and at subsequent said threshold level;

(d) locating new regions of pixels recognizable above the subsequent threshold level in the target images at the first of preset intensities;

(e) locating coincident regions of pixels recognizable above the subsequent threshold level that incorporate the regions of pixels recognizable above the first threshold level located in said step (b);

(f) adding number of the new and coincident regions of pixels of preset sizes located in said steps (d) and (e) to record a final number of the preset sizes of regions of pixels recognizable above the threshold levels at the first of preset intensities; and (h) repeating said steps (a), (b), (c), (d), (e), (f) and (g) at subsequent preset intensities.

Figure 5:
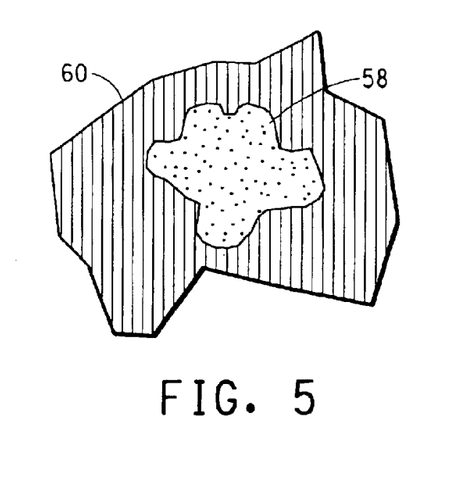
Figure 6:
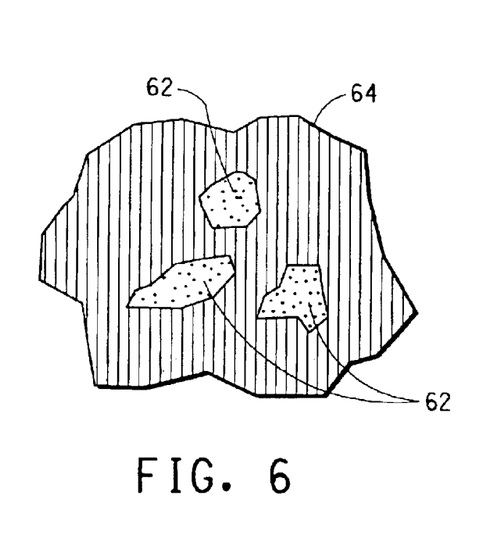
Figure 7:
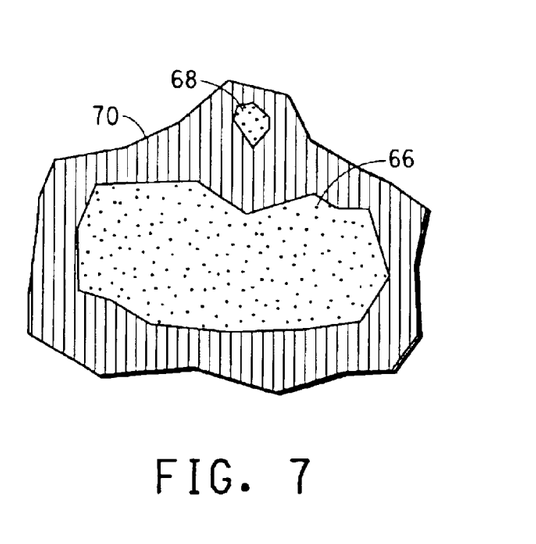

In the foregoing method steps (a) through (h), several decisions are made on the basis of preset criteria. One example is shown in FIGS. 4, 5, 6 and 7. In step (a), when the target images at first of the preset intensities and at first of threshold levels is scanned, i.e., at the highest threshold level, only regions of pixels representing flakes having most prominent visible features would be located. The location and size, in accordance with the preset criteria of sizes, such a region is recorded as a new flake, shown in FIG. 4. When the same portion of the target image is scanned in step (c) at subsequent threshold level, it is possible that new regions of pixels could become recognizable above the subsequent threshold level in the target images at the first of preset intensities. Thus, a previously located region 58 recorded as new flake may appear larger once its additional features 60 are located at lower threshold level, as seen in FIG. 5. The foregoing coincident regions include single contiguous regions of pixels recognizable above the first threshold level that are enveloped within single regions of pixels recognizable above said subsequent threshold level, such as the one in seen in FIG. 5. Under such a scenario the previously located and recorded size of the flake is discarded and the new larger size is recorded in its place.

Alternatively, the foregoing coincident regions can also include plurality of regions of pixels recognizable above the first threshold level that are merged within regions of pixels recognizable above the subsequent threshold level. Thus, a cluster of small regions 62 in FIG. 6, which were previously located and recorded as new flakes of small size, when analyzed at lower threshold level can be part of a larger flake 64. Under such a scenario, the previously located and recorded size of these small regions is discarded and a new larger region is located and recorded in their place. In addition, in another scenario, at a higher threshold level, a larger region 66 could be located adjacent to a smaller region 68 shown in FIG. 7, both of which would be located and recorded. However, the same combination, when viewed at a lower threshold level can become part of a larger region 70. Under such a scenario, the previously located and recorded sizes of these smaller/larger regions 66 and 68 are kept and larger region 70 is discarded, since larger region 70 is likely to be a result of multiple flakes appearing as one merged flake, which should not, therefore, be counted as one large flake but should be counted as two distinct regions, namely larger region 66 and smaller region 68. In addition to the foregoing, it is possible that a region not recorded at all at higher threshold could appear at lower threshold, which would also be located and recoded at that threshold level. Moreover, it would be apparent that any regions having no changes to their size even at lower threshold levels would be also located and recorded without change. The same process is repeated at other preset intensities, and, if desired, device 1 can be repositioned at other portions of target coating 2 to get additional data on the flake characteristics of unknown flakes 6.

Applicants discovered that in order to match the flake characteristics of unknown flakes 6 to that of known flakes, one must not only determine the flake concentration of various sizes present in unknown coating 2, but one must also determine the sparkle they impart to coating 2. By locating and recording the number of flakes from the target images at higher and lower thresholds and multiple illumination levels, applicants took into account not only the sparkle provided by unknown flakes 6 but also their concentration in coating 2. Applicants' unexpected discovery of the foregoing extraction method is unique.

Once the forgoing step (iii) is accomplished, the process includes:

(iv) Correlating the characteristics of unknown metallic flakes 6 in the target image to stored characteristics of known metallic flakes at the preset intensity to identify one or more said known metal flakes that match the characteristics of unknown metallic flakes 6. The foregoing step (iv) includes several of the following sub-steps:

(a) comparing the characteristic of unknown metallic flakes 6 of the preset size to the benchmark characteristic of the known metallic flakes of same preset size extracted from a benchmark coating on a first panel containing the known metal flakes to determine a feature distance for each preset intensity;

(b) adding the feature distances for all the preset intensities to arrive at a sum of the feature distances for the preset size;

(c) multiplying the sum with a weight factor to calculate a weighted feature distance for said preset size;

(d) repeating said steps (a), (b) and (c) for all other said preset sizes to determine weighted feature distances for other said preset sizes;

(e) adding the weighted feature distances for the preset sizes to arrive at a final feature distance for the coating on the first panel;

(f) repeating said steps (a), (b), (c), (d) and (e) to determine the final feature distances from benchmark coatings on other panels;

(g) selecting shortest final feature distances from the final feature distances; and (h) identifying the known flake or a blend of the known flakes from the benchmark coatings on the panels having said shortest final feature distances.

Once the forgoing step (iv) is accomplished, the method includes:

(v) Displaying the identified one or more known metal flakes that match the characteristics of unknown metallic flakes 6 on screen 22 of computer 11. If desired, the foregoing steps can be repeated at other target portions of target coating 2 for greater accuracy in matching the unknown metallic flakes 6 with the known metallic flakes.

Alternatively, one could transmit the information via a website or e-mail to an offsite location; store information on a computer memory or a portable memory device, such as a floppy disc; or send the information to a printer in communication with computer 11 to print out the information.

As stated before, the method of the present invention utilizes a database of a very small number of benchmark panels that are coated with known metallic flakes or a known combination of metallic flakes to reproduce the benchmark coatings described earlier. Device 1 can be conveniently used to determine the benchmark characteristics of the known metallic flakes in the benchmark coatings. The method used is similar as that described earlier, which includes the following steps:

(i) sequentially directing one or more beams of light at at least two the preset intensities towards a benchmark portion of benchmark the coating on said first panel;

(ii) directing a reflection of the benchmark portion of the benchmark coating on the first panel to photosensitive surface 2A to sequentially capture benchmark images of the benchmark portion of the benchmark coating on the first panel;

(iii) sequentially measuring the benchmark characteristics of the known metallic flakes in the images at the preset intensities; and (iv) saving the benchmark characteristics of the known metallic flakes in the benchmark images in a database, in a CD-ROM, hard drive of a computer, or in a host computer in communication with a client computer.

In the foregoing, step (iii) further includes:

(a) scanning the benchmark images at first of the preset intensities and at first of the threshold levels;

(b) locating regions of pixels recognizable above the first threshold level in the benchmark images at the first of the preset intensities;

(c) scanning the benchmark images at the first of the preset intensities and at the subsequent threshold level;

(d) locating new regions of pixels recognizable above the subsequent threshold level in the benchmark images at the first of preset intensities;

(e) locating coincident regions of pixels recognizable above the subsequent threshold level that incorporate the regions of pixels recognizable above the first threshold level located in step (b);

(f) adding a number of the new and coincident regions of pixels of preset sizes located in the steps (d) and (e) to record a final number of the preset sizes of regions of pixels recognizable above the threshold levels at the first of preset intensities; and (h) repeating the steps (a), (b), (c), (d), (e), (f) and (g) at subsequent said preset intensities.

In the foregoing, the preset sizes are the same as those described earlier. Thus, the applicants have discovered that the use of a small number of the benchmark panels, which are economical to produce, is sufficient for characterizing most of the unknown metallic flakes typically used, for example, in refinish auto industry.

By way of example, applicants determined that typically about 8 types of aluminum metal flakes supplied by various venders are used in the automotive refinish finish. Sometimes, the metallic paints can include more than one type of aluminum flake, typically a mixture of two types of aluminum flakes. Thus, in addition to 8 single flake type paints there would exist 28 possible combinations of paints that contain 2 flake types from a population of 8 flake types. Applicants have determined that 5 of these combinations are never used such as, a combination of very bright and very dull flake. In order to minimize effect of any other components of paints on the metallic flake characterization, same other components of paint, such as binders, solvents, were used in the Chromabase® line of metallic refinish paints supplied by DuPont Company, Wilmington, Del. Single blue pigment was used in combination with metallic flakes. Thus, the following parts by weight of the flake/pigment combinations were used:

10/90

25/75

50/50

75/25

90/10

It should be noted that any other flake/pigment combination would also be suitable. In addition, the following parts by weight of the flake of one type/flake of other type combinations were used:

25/75

50150

75/25

It should be noted that any other flake of one type/flake of other type combinations would also be suitable. Thus, the total number of different paint combinations containing various metallic flake combinations and flake/pigment combinations include:

(23 two-flake combinations)×(5 flake/pigment combinations)×(3 flake of one type/flake of other type combinations)=345

(8 single flakes)×(5 flake/pigment combinations)=40

Total number of paints of known formulations used=385

These paints were applied by conventional application techniques, such as spray application, over steel panels to a cured film thickness of 25 micrometers (1 mil) to produce 385 benchmark panels. It should be noted that the present database is just one example of how the benchmark panels can be used. One skilled in the art would recognize that the foregoing database can be expanded to further improve the accuracy of characterization of unknown metallic flakes in paints or the database can be reduced, if less accuracy is sufficient for the purpose.

Each of these benchmark panels were imaged by using device 1 in manner described earlier at 25 target portions on each of these benchmark panels at three preset intensity levels of 19.6%, 31.4% and 39.2%. It should be noted that one would have to use the same preset intensity levels in characterizing the unknown metallic flakes, as those used in producing the database of the benchmark panels, which is stored in computer 11. Since, the same method used for producing the database of the benchmark panels is also used for characterizing the unknown metallic flakes, any process variations between the two processes is eliminated, thereby resulting in far better accuracy in characterizing the unknown metallic flakes.

The method of the present invention can be also extended, if desired, to characterizing an unknown pigment of the target metallic coating by using an imaging device that can store a target image in color and in gray scale. The gray scale image is used to characterize the unknown metallic flake and the color image is used to characterize the unknown pigment. Thus the method can further include:

(i) transforming RGB data of the target color images into L,a,b data;

(ii) accessing from a color formula database one or more color formulas that match the L,a,b data;

(iii) displaying the color formulas on a screen of a computer; and (vi) selecting a desired color formula from the color formulas.

It should be noted that the method for getting RGB data and L,a,b data is very well known. The foregoing method can further include displaying identification criteria of the color formulas on the screen. Typical identification criteria include one or more of a manufacturer's name, make, model, year of production, color name, paint code, cross reference information, intended use, VIN number, or spectrophotometric data of a vehicle or its color.

If desired, in the method of the present invention computer 11 is a client computer in communication, such as via a website, modem, or via server, with a host computer, which can be in a remote location any where in the world or at suppliers' place of business. Under such a scenario, the target images whether in gray scale or in color can reside on the client computer and the color formula database and the database of the benchmark panels reside on the host computer in communication with the client computer or in a memory device, such as a CD-ROM or the hard drive of the client computer. In still another scenario, the target images whether in gray scale or in color, the color formula database and the benchmark panels all reside on the host computer in communication with the client computer, where the images of target portion 2A are sent to the host computer, which then sends back the client computer the three closest matches described earlier.

What is claimed is:

1. A device for characterizing a target coating containing unknown metallic flakes comprising:

(i) means for positioning said device over said target coating;

(ii) means for producing one or more beams of light at one or more preset intensities;

(iii) means for imaging;

(iv) means for directing said beams of light towards a target portion of said target coating;

(v) means for directing a reflection of said target portion to a photosensitive surface located in said means for imaging to capture a target image of said portion;

(vi) means for measuring characteristics of said metallic flakes in said target image at said preset intensity;

(vii) means for correlating said characteristics of said unknown metallic flakes in said target image to stored characteristics of known metallic flakes at said preset intensity to identify one or more said known metal flakes that match said characteristics of said unknown metallic flakes; and (viii) means for displaying said identified one or more known metal flakes that match said characteristics of said unknown metallic flakes.

2. The device of claim 1 wherein said means (i), (ii), (iii), (iv) and (v) are positioned in a housing wherein said means (iii) are located opposite of said means (i) and wherein a beam splitter comprising said means (iv) and (v) is positioned between said means (i) and (iii) and wherein said means (ii) are positioned adjacent to said beam splitter to direct said beams at an angle normal to said target portion.

3. The device of claim 1 wherein said means (ii) comprise means (viii) for collimating said one or more beams of light.

4. The device of claim 1 where said means (iii) comprise means (ix) for focusing said reflection of said target portion on said photosensitive surface.

5. The device of claim 1 wherein said means (iii) comprise an imaging device suitable for producing said target images as gray target images.

6. The device of claim 5 wherein a footprint of said gray target images produced by said imaging device range from about 0.01 millimeters square to about 25.0 millimeters square.

7. The device of claim 5 wherein said gray target images are digitized in ranges from 40,000 pixels to 16,000,000 pixels wherein each said pixel is capable of recognizing 16 to 65,536 levels of light intensities.

8. The device of claim 7 wherein each said pixel is capable of recognizing 256 levels of said light intensities.

9. The device of claim 1 wherein said means (iii) comprise an imaging device suitable for producing said target images as gray target images or as color target images.

10. The device of claim 9 wherein a footprint of said gray and color target images digitized by said imaging device range from about 0.01 millimeters square to about 25.0 millimeters square.

11. The device of claim 9 wherein said gray and color target images are digitized in ranges from 40,000 pixels to 16,000,000 pixels wherein each said pixel is capable of recognizing 18 to 65,536 levels of light intensities for each of three primary color channels.

12. The device of claim 5 or 9 wherein said means (vi) comprise:
(a) means for scanning said target images above threshold levels at said preset intensities;
(b) means for locating regions of pixels recognizable in said target images above said threshold levels and at said preset intensities; and
(c) means for recording number of preset sizes of regions of pixels recognizable above said threshold levels at said preset intensities.

13. The method of claim 12 wherein said preset sizes of said regions of pixels comprise small, medium, large, extra large zones, clusters of zones, or a combination thereof.

14. The device of claim 13 wherein said small zone ranges from about 49 to about 83 micrometers square, wherein said medium zone ranges from about 127 to about 239 micrometers square, wherein said large zone ranges from about 342 to about 576 micrometers square, wherein said extra large zone ranges from about 577 to about 122500 micrometers square, and wherein said cluster zones range from about 49 micrometers square to about 122500 micrometers square.

15. The device of claim 1 wherein said means (vii) comprise:
(a) means for comparing said characteristic of said unknown metallic flakes of said preset size to said benchmark characteristic of said known metallic flakes of same preset size extracted from a benchmark coating on a first panel containing said known metal flakes to determine a feature distance for each said preset intensity;
(b) means for adding said feature distances for all said preset intensities to arrive at a sum of said feature distances for said preset size;
(c) means for multiplying said sum with a weight factor to calculate a weighted feature distance for said preset size;
(d) means for repeating said steps (a), (b) and (c) for all other said preset sizes to determine weighted feature distances for other said preset sizes;
(e) means for adding said weighted feature distances for said preset sizes to arrive at a final feature distance for said coating on said first panel;
(f) means for repeating said steps (a), (b), (c), (d) and (e) to determine said final feature distances from benchmark coatings on other panels;
(g) means for selecting shortest final feature distances from said final feature distances; and
(h) means for identifying said known flake or a blend of said known flakes from said benchmark coatings on said panels having said shortest final feature distances.

16. The device of claim 1 wherein said target coating is applied over surface of an automotive body.

17. A method for characterizing a target coating containing unknown metallic flakes comprising:
(i) directing one or more beams of light at a put intensity towards a target portion of said target coating;
(ii) directing a reflection of said portion to a photosensitive surface to capture a target image of said target portion;
(iii) measuring characteristics of said unknown metallic flakes in said target image at said preset intensity;
(iv) correlating said characteristics of said unknown metallic flakes in said target image to stored characteristics of known metallic flakes at said preset intensity to identify one or more said known metal flakes that match said characteristics of said unknown metallic flakes; and
(v) displaying said identified one or more known metal flakes that match said characteristics of said unknown metallic flakes.

18. The method of claim 17 further comprising repeating said steps (i), (ii), and (iii) at other preset intensities.

19. The method of claim 17 or 18 further comprising repeating said steps (i), (ii), (iii) and (iv) at other target portions of said target coating.

20. The method of claim 17 wherein said target coating comprises polymers, pigments, and additives.

21. The method of claim 20 wherein said pigments comprise light absorbing pigments, light scattering pigments, light interference pigments, light reflecting pigments, or a combination thereof.

22. The method of claim 17 wherein said target coating is affixed to surface of an automotive body.

23. A method for characterizing a target coating containing unknown metallic flakes comprising:
(i) sequentially directing one or more beams of light at at least two preset intensities towards a target portion of said target coating;
(ii) directing a reflection of said portion to a photosensitive surface to sequentially capture target images of said target portion at said preset intensities;
(iii) sequentially measuring characteristics of said unknown metallic flakes in said target images;
(iv) correlating said characteristics of said unknown metallic flakes in said target images to benchmark characteristics of known metallic flakes at said preset intensities to identify one or more said known metal flakes that match said characteristics of said unknown metallic flakes; and
(v) displaying said identified one or more known metal flakes that match said characteristics of said unknown metallic flakes.

24. The method of claim 23 wherein said target images on said photosensitive surface are in gray scale.

25. The method of claim 23 wherein said beam is collimated.

26. The method of claim 23 wherein in said step (i) said beam is directed at an angle normal to said target portion.

27. The method of claim 23 wherein said photosensitive surface is a charged couple device sensor of an imaging device that captures said target image.

28. The method of claim 23 wherein said step (iii) comprises:
   (a) scanning said target images at first of said preset intensities and at first of threshold levels;
   (b) locating regions of pixels recognizable above said first threshold level in said target images at said first of said preset intensities;
   (c) scanning said target images at said first of said preset intensities and at subsequent said threshold level;
   (d) locating new regions of pixels recognizable above said subsequent threshold level in said target images at said first of preset intensities;
   (e) locating coincident regions of pixels recognizable above said subsequent threshold level that incorporate said regions of pixels recognizable above said first threshold level located in said step (b);
   (f) adding number of said new and coincident regions of pixels of preset sizes located in said steps (d) and (e) to record a final number of said preset sizes of regions of pixels recognizable above said threshold levels at said first of preset intensities; and (h) repeating said steps (a), (b), (c), (d), (e), (f) and (g) at subsequent said preset intensities.

29. The method of claim 28 wherein said coincident regions comprise:
   (i) single contiguous regions of pixels recognizable above said first threshold level that are enveloped within single regions of pixels recognizable above said subsequent threshold level; and
   (ii) plurality of regions of pixels recognizable above said first threshold level that are merged within regions of pixels recognizable above said subsequent threshold level.

30. The method of claim 28 wherein said preset sizes of said regions of pixels comprise small, medium, large, extra large zones; clusters of zones or a combination thereof.

31. The method of claim 30 wherein said small zone ranges from about 49 to about 83 micrometers square, wherein said medium zone ranges from about 127 to about 239 micrometers square, wherein said large zone ranges from about 342 to about 576 micrometers square, wherein said extra large zone ranges from about 577 to about 122500 micrometers square, and wherein said cluster zones range from about 49 micrometers square to about 122500 micrometers square.

32. The method of claim 23 wherein said step (iv) comprises
   (a) comparing said characteristic of said unknown metallic flakes of said preset size to said benchmark characteristic of said known metallic flakes of same preset size extracted from a benchmark coating on a first panel containing said known metal flakes to determine a feature distance for each said preset intensity;
   (b) adding said feature distances for all said preset intensities to arrive at a sum of said feature distances for said preset size;
   (c) multiplying said sum with a weight factor to calculate a weighted feature distance for said preset size;
   (d) repeating said steps (a), (b) and (c) for all other said preset sizes to determine weighted feature distances for other said preset sizes;
   (e) adding said weighted feature distances for said preset sizes to arrive at a final feature distance for said coating on said first panel;
   (f) repeating said steps (a), (b), (c), (d) and (e) to determine said final feature distances from benchmark coatings on other panels;
   (g) selecting shortest final feature distances from said final feature distances; and
   (h) identifying said known flake or a blend of said known flakes from said benchmark coatings on said panels having said shortest final feature distances.

33. The method of claim 32 wherein said benchmark characteristics of said known metallic flakes in said benchmark coatings on said panels are ascertained by the steps comprising
   (i) sequentially directing one or more beams of light at at least two said preset intensities towards a benchmark portion of benchmark said coating on said first panel;
   (ii) directing a reflection of said benchmark portion of said benchmark coating on said first panel to a photosensitive surface to sequentially capture benchmark images of said benchmark portion of said benchmark coating on said first panel;
   (iii) sequentially measuring said benchmark characteristics of said known metallic flakes in said images at said preset intensities; and
   (iv) saving said benchmark characteristics of said known metallic flakes in said benchmark images in a database, in a CD-ROM, hard drive of a computer, or in a host computer in communication with a client computer.

34. The method of claim 32 wherein said step (iii) comprises:
   (a) scanning said benchmark Images at first of said preset intensities and at first of threshold levels;
   (b) locating regions of pixels recognizable above said first threshold level in said benchmark images at said first of said preset intensities;
   (c) scanning said benchmark images at said first of said preset intensities and at subsequent said threshold level;
   (d) locating new regions of pixels recognizable above said subsequent threshold level in said benchmark images at said first of preset intensities;
   (e) locating coincident regions of pixels recognizable above said subsequent threshold level that incorporate said regions of pixels recognizable above said first threshold level located in said step (b);
   (f) adding number of said new and coincident regions of pixels of preset sizes located in said steps (d) and (e) to record a final number of said preset sizes of regions of pixels recognizable above said threshold levels at said first of preset intensities; and
   (h) repeating said steps (a), (b), (c), (d), (e), (f) and (g) at subsequent said preset intensities.

35. The method of claim 34 wherein said coincident regions comprise:
   (i) single contiguous regions of pixels recognizable above said first threshold level that are enveloped within single regions of pixels recognizable above said subsequent threshold level; and (ii) plurality of regions of pixels recognizable above said first threshold level that are merged within regions of pixels recognizable above said subsequent threshold level.

36. The method of claim 34 wherein said preset sizes of said known metallic flakes comprise small, medium, large, extra large metallic flakes; clusters of metallic flakes or a combination thereof.

37. The method of claim 36 wherein size of said small flake ranges from about 49 to about 83 micrometers square, wherein size of said medium flake ranges from about 127 to about 239 micrometers square, wherein size of said large flake ranges from about 342 to about 576 micrometers square, wherein size of said extra flake ranges from about 577 to about 122500 micrometers square, and wherein size of said clusters range from about 49 micrometers square to about 122500 micrometers square.

38. The method of claim 34 wherein said benchmark coatings on said panels comprise polymers, pigments, and additives.

39. The method of claim 34 wherein said pigments comprise light absorbing pigments, light scattering pigments, light interference pigments, light reflecting pigments, or a combination thereof.

40. The method of claim 23 wherein said target coating comprises polymers, pigments, and additives.

41. The method of claim 40 wherein said pigments comprise light absorbing pigments, light scattering pigments, light interference pigments, night reflecting pigments, or a combination thereof.

42. The method of claim 23 wherein said present intensities are fixed at three illumination levels.

43. The method of claim 23 wherein said wherein said photosensitive surface is a charged couple device sensor of an imaging device that captures said target images in gray target images.

44. The method of claim 23 wherein said wherein said photosensitive surface is a charged couple device sensor of an imaging device that captures said target images in gray target images or in color target images.

45. The method of claim 44 wherein a footprint of said gray and said color target images captured by said imaging device range from about 0.01 millimeters square to about 25.0 millimeters square.

46. The method of claim 45 further comprising:
(i) transforming RGB data of said target color images into L,a,b data;
(ii) accessing from a color formula database one or more color formulas that match said L,a,b data;
(iii) displaying said color formulas on a screen of a computer; and
(vi) selecting a desired color formula from said color formulas.

47. The method of claim 46 further comprising displaying identification criteria of said color formulas on said screen.

48. The method of claim 47 wherein said identification criteria comprise one or more of a manufacturer's name, make, model, year of production, color name, paint code, cross reference information, intended use, VIN number, or spectrophotometric data of a vehicle or its color.

49. The method of claim 48 wherein said computer is a client computer in communication with a host computer.

50. The method of claim 49 wherein said target color images reside on said client computer and said color formula database resides on said host computer.

51. A method for characterizing a target coating containing unknown metallic flakes comprising:
(i) directing sequentially a collimated beam of light at three preset intensities upon a target portion of said target coating at a normal angle;
(ii) directing a reflection of said coated surface to a photosensitive surface to sequentially capture images in a gray scale of said target portion at said preset intensities at said three preset intensities;
(iii) sequentially measuring characteristics of said unknown metallic flakes in said target images;
(iv) correlating said characteristics of said unknown metallic flakes in said target images to benchmark characteristics of known metallic flakes at said preset intensities to identify three said known metal flakes that match said characteristics of said unknown metallic flakes;
(v) displaying said identified one or more known metal flakes that match said characteristics of said unknown metallic flakes.

52. A method for producing a metallic flake containing coating composition, wherein a coating therefrom matches characteristics of a target coating containing unknown metallic flakes, said method comprising:
(i) directing one or more beams of light et a preset intensity towards a target portion of said target coating;
(ii) directing a reflection of said portion to a photosensitive surface to capture a target image of said target portion;
(iii) measuring characteristics of said unknown metallic flakes in said target image at said preset intensity;
(iv) correlating said characteristics of said unknown metallic flakes in said target image to stored characteristics of known metallic flakes at said preset intensity to identify one or more said known metal flakes that match said characteristics of said unknown metallic flakes;
(v) displaying said identified one or more known metal flakes that match said characteristics of said unknown metallic flakes;
(vi) preparing one or more test coating compositions containing said identified known metal flakes;
(vii) applying said test coating compositions over test substrates to produce test coatings thereon;
(vii) comparing said test coatings against said target coating to select test coating having characteristics that match said characteristics of said target coating; and
(viii) selecting test coating composition that produces said matched test coating.

* * * * *